United States Patent
Lancisi et al.

[11] Patent Number: 6,149,683
[45] Date of Patent: Nov. 21, 2000

[54] POWER SYSTEM FOR AN IMPLANTABLE HEART PUMP

[75] Inventors: David M. Lancisi; Raymond G. Gauthier, both of Folsom; Richard K. Wampler, Granite Bay, all of Calif.

[73] Assignee: Kriton Medical, Inc., Sacramento, Calif.

[21] Appl. No.: 09/166,539

[22] Filed: Oct. 5, 1998

[51] Int. Cl.[7] .................................................. A61M 1/10
[52] U.S. Cl. ............................................... 623/3; 600/16
[58] Field of Search .......................... 623/3; 600/16–17; 417/423.7, 423.14, 16, 411; 607/34, 33, 61

[56] References Cited

U.S. PATENT DOCUMENTS

| | | |
|---|---|---|
| 3,518,997 | 7/1970 | Sessions . |
| 3,620,220 | 11/1971 | Murphy, Jr. . |
| 3,738,371 | 6/1973 | Raddi et al. . |
| 3,757,795 | 9/1973 | Anderson . |
| 3,783,877 | 1/1974 | Bowers . |
| 4,102,344 | 7/1978 | Conway et al. . |
| 4,134,408 | 1/1979 | Brownlee et al. . |
| 4,173,796 | 11/1979 | Jarvik . |
| 4,346,335 | 8/1982 | McInnis . |
| 4,441,210 | 4/1984 | Hochmair et al. . |
| 4,590,941 | 5/1986 | Saulson et al. ............................ 607/34 |
| 4,662,358 | 5/1987 | Farrer et al. ................................ 623/3 |
| 4,692,145 | 9/1987 | Weyant ..................................... 604/65 |
| 4,944,748 | 7/1990 | Beamm et al. .............................. 623/3 |
| 4,957,504 | 9/1990 | Chardack ..................................... 623/3 |
| 5,049,134 | 9/1991 | Golding et al. . |
| 5,129,789 | 7/1992 | Thornton et al. . |
| 5,290,227 | 3/1994 | Pasque . |
| 5,317,220 | 5/1994 | Godkin . |
| 5,321,392 | 6/1994 | Skakoon et al. ......................... 340/636 |
| 5,358,514 | 10/1994 | Schulman et al. . |
| 5,405,367 | 4/1995 | Schulman et al. . |
| 5,470,208 | 11/1995 | Kletschka ..................................... 623/3 |
| 5,569,156 | 10/1996 | Mussivand ................................. 623/3 |
| 5,613,935 | 3/1997 | Jarvik . |
| 5,676,651 | 10/1997 | Larson, Jr. et al. . |
| 5,697,953 | 12/1997 | Kroll et al. . |
| 5,722,930 | 3/1998 | Larson, Jr. et al. . |
| 5,769,877 | 6/1998 | Barreras, Sr. . |

OTHER PUBLICATIONS

M. Arabia, et al. "A New Automatically Controlled Electric Tah", *Trans Am Soc Artif Intern Organs*, vol. XXVI, pp. 60–65 (1980).

P. J. Miller et al. "In Vivo Evaluation of a Compact, Implantable Left Ventricular Assist System (LVAS)", *Trans Am Soc Artif Intern Organs*, vol. XXIX, pp. 551–555 (1983).

D.B. Gernes, et al. "Development of an Implantable, Integrated, Electrically Powered Ventricular Assist System", *Trans Am Soc Artif Intern Organs*, vol. XXIX, pp. 546–550 (1983).

(List continued on next page.)

*Primary Examiner*—Bruce Snow
*Attorney, Agent, or Firm*—George H. Gerstman; Seyfarth, Shaw

[57] ABSTRACT

A power system for an implantable heart pump is provided. The system includes two batteries, a microprocessor controller, two motor drivers, a multiplexer, two stators and a TET coil. During normal operation, only one battery and one motor driver are in use at a time to drive both stators.

6 Claims, 1 Drawing Sheet

OTHER PUBLICATIONS

G. Rosenberg et al., "An Electric Motor–Driven Total Artificial Heart: Seven Months Survival in the Calf", *Trans Am Soc Artif Intern Organs*, vol. XXV, pp. 69–71 (1984).

J. Moise et al., "Experimental Evaluation of Complete Electrically Powered Ventricular Assist System", *Trans Am Soc Artif Intern Organs*, vol. XXXI, pp. 202–205 (1985).

Jal S. Jassawalla et al., "In Vitro and In Vivo Testing of a Totally Implantable Left Ventricular Assist System", *Trans Am Soc Artif Intern Organs*, vol. XXXIV, pp. 470–475 (1988).

Narayanan Ramasamy et al, "Chronic Ovine Evaluation of a Totally Implantable Electrical Left Ventricular Assist System", *Trans Am Soc Artif Intern Organs*, vol. XXVV, PP. 402–404.

William J. Weiss et al., "In Vivo Performance of a Transcutaneous Energy Transmission System with the Penn State Motor Drive Ventricular Assist Device", *Trans Am Soc Artif Intern Organs*, vol. XXXV, pp. 284–288.

Tofy Mussivand, et al., "In Vitro and In Vivo Performance Evaluation of a Totally Implantable Electrohydraulic Left Ventricular Assist System", *Trans Am Soc Artif Intern Organs*, vol. XXXV, pp. 433–435.

Innovative Ventricular Assist System (IVAS), RFP NHL-BI–HV–94–25, pp. 47–53 (1994).

Innovative Ventricular Assist System (IVAS), RFP NHL-BI–HV–94–25, pp. 23–24 (1994).

POWER SYSTEM FOR AN IMPLANTABLE HEART PUMP

FIELD OF THE INVENTION

The present invention concerns a novel power system for an implantable heart pump.

BACKGROUND OF THE INVENTION

A most important consideration with implanted artificial heart pumps and their associated control and power systems are reliability and safety. They must be capable of working properly for extended periods of time without replacement of implanted parts. All parts and systems as used must be biocompatible. They must be capable of use without impeding the proper circulation and functioning of blood through clotting or cell damage.

Also of great importance are quality of patient life considerations. The implanted pump and control and power system must be small and preferably without any wires or other structures protruding through the skin. The system must interfere with normal patient activities to the minimum extent possible. Therefore, the system should be capable of functioning for at least limited periods of time with untethered operation so that the patient may bathe comfortably and engage in other activities. Any external components must be easy and comfortable for the patient to use on his own.

One major consideration relates to redundancy in the power and control system. A certain amount of redundancy especially as to parts, such as batteries and motors, is essential in order that the system meet safety requirements. Therefore, systems that lack any redundancy are not considered acceptable. On the other hand, too much redundancy even including those components extremely unlikely to fail can add unnecessary size, complexity and cost to a system.

It is therefore an object of the present invention to provide a power and control system that is reliable and safe, without requiring unnecessary redundancy. The advantages of the present invention will become apparent as the description proceeds.

SUMMARY OF THE INVENTION

In accordance with the present invention, a novel implantable blood pump is provided. The pump includes a pump housing, a rotor mounted for rotation within the housing with the rotor having an elongated shaft portion and an impeller, and first and second stators for aiding in rotation of the impeller. A stator driver is provided for, driving the stators. The pump also includes a microprocessor, and first and second batteries. The batteries, microprocessor and driver are interconnected and programmed so that during normal operation only one of the batteries is in use at a time for powering both stators simultaneously.

As used herein, a "battery" comprises a single sell or plurality of cells which are connected together to operate as a unit.

In the illustrative embodiment, the driver comprises two stator drivers. A multiplexer is provided for coupling the drivers to the stators in a desired manner, although it is preferred that only one driver be used during normal operation for driving both stators.

In the illustrative embodiment, the system includes an external transcutaneous energy transmission coil and an external power source. The system may also include an external monitor.

In one embodiment, the invention concerns a method for controlling the drive system for an electrical, implantable heart pump. It includes the steps of providing first and second batteries, a microprocessor, a transcutaneous energy transmission coil, a driver, and first and second stators, and using only one of the batteries at a time during normal operation of the system to power both stators simultaneously.

A more detailed explanation of the invention is provided in the following description and claims and is illustrated in the accompanying drawing.

DETAILED DESCRIPTION OF THE ILLUSTRATIVE EMBODIMENT

The control system of the present invention may be used with an implantable heart pump such as the heart pump disclosed in Wampler U.S. patent application Ser. No. 08/910,375, filed Aug. 13, 1997, the disclosure of which is incorporated herein. One example of an implantable heart pump with two stators is the FIGS. 11–14 embodiment of application Ser. No. 08/910,375. It is understood, however, that no limitation is intended with respect to the particular heart pump to which the present control system is applicable.

Figure 1:
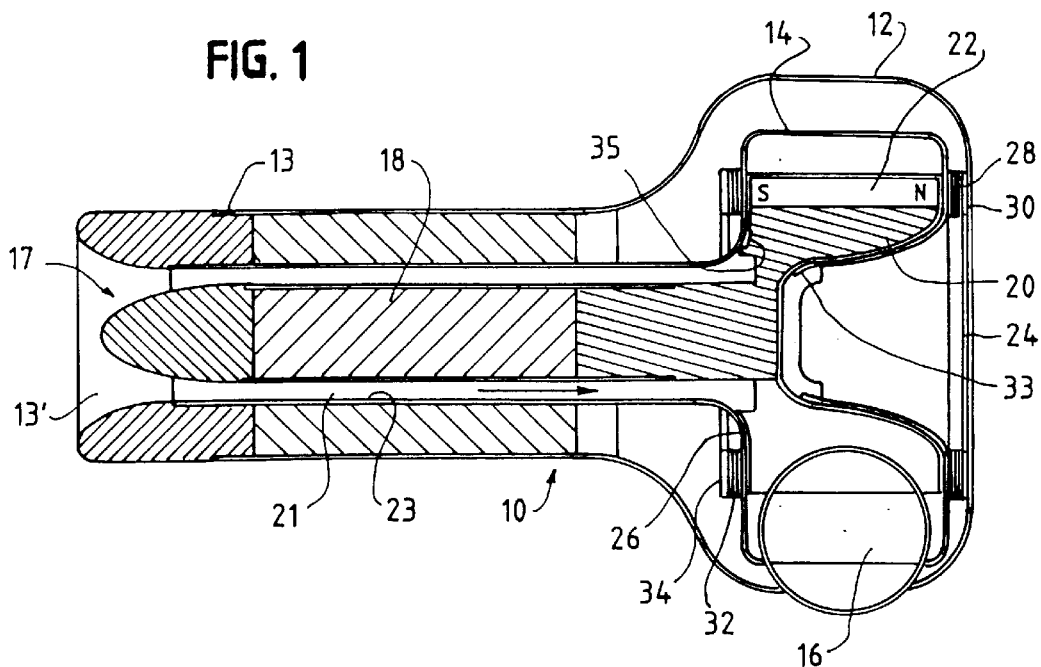
FIG. 1 is a longitudinal, cross-sectional view of a schematic representation of an implantable heart pump for use in association with the control system of the present invention.

As illustrated in FIG. 1, a rotary blood pump 10 includes housing 12, having an elongated inlet tube 13 with an entry end 13' and an impeller casing or volute 14. A discharge tube 16 extends through the housing to communicate with the interior periphery of casing 14. Tube 16 has a tangential orientation with respect to the radius of the casing, for effectively channeling the blood output from the pump to an impeller 20. There is a blood flow path 21 between rotor 17 and the inner sidewalls 23 of inlet tube 13.

Rotor 17 is mounted for rotation about a longitudinal axis which extends both through shaft 18 and impeller 20. Although this embodiment includes an impeller and a casing of centrifugal design, the present invention may also be adapted advantageously to rotary blood pumps of axial flow design or other types of blood pumps.

Impeller 20 has a number of blade sectors that are relatively thick in the axial direction. This thick impeller 20 has the ability to utilize magnetic pieces 22 that are inserted in a manner enabling a pair of stators 24 and 26 to be on opposite sides of the impeller. A first motor stator 24, comprising conductive coils or motor windings 28 and back iron ring 30, is located at the rear of impeller 20. A ring of back iron 30 is located behind windings 28. First motor stator 24 is fixed between housing 12 and casing 14.

A second motor stator 26, comprising windings 32 and back iron 30, is positioned on the forward side of impeller 20. Windings 32 are fixed to casing 14 and a ring of back iron 34 is positioned forward of windings 32.

Magnetic bearings (not shown) are provided for levitating rotor 17 and maintaining it in proper radial alignment with respect to its longitudinal axis. Hydrodynamic bearings 33 and 35 are provided to constrain axial motion and to provide radial support in the case of eccentric motion or shock on the device.

Among other things, the dual stator design using motor stators 24 and 26 is adapted to provide system redundancy for a fail-safe mode, since each stator can be made to operate independently of the other in the case of a failure. However, during normal operation both stators 24 and 26 are driven simultaneously.

Figure 2:
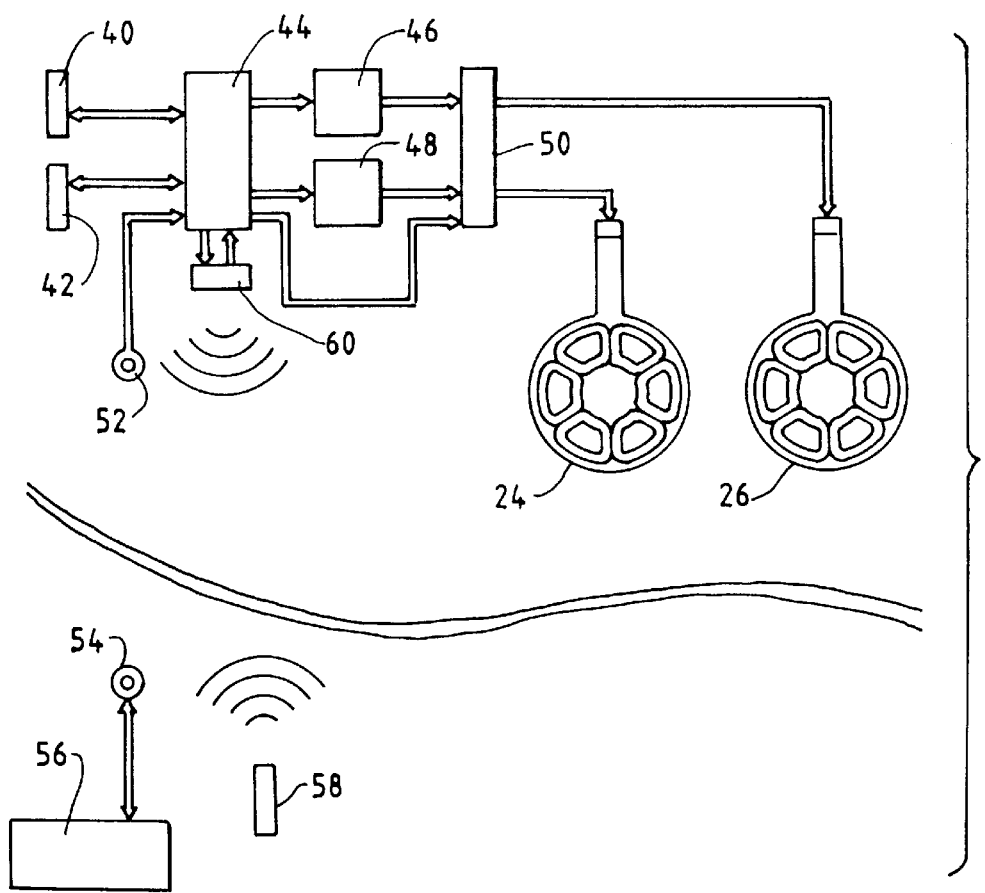
FIG. 2 comprises a block diagram of a control system for an electrical, implantable heart pump constructed in accordance with the principles of the present invention.

FIG. 2 illustrates a control system for an electric, implantable heart pump, such as but not limited to the heart pump disclosed herein and illustrated in FIG. 1.

Referring to the drawing, two batteries 40, 42 are connected to inputs of the microprocessor controller 44. The batteries 40, 42 provide a rechargeable power source for the implanted system. The microprocessor controller 44 is an overall implanted system controller.

The microprocessor controller 44 is connected to two motor drivers 46, 48. Alternatively, a single motor driver could be used for driving both stators. The motor drivers 46, 48 and the microprocessor controller 44 are connected to a multiplexer 50. The multiplexer is a flexible switch matrix capable of connecting motor coils of dual stators 24 and 26 to motor drivers 46, 48 in any manner desired. The stators 24 and 26 provide a motor coil configuration that provides torque to rotate the impeller of an implantable heart pump.

The implanted system also includes a transcutaneous energy transmission (TET) coil 52 controlled by the microprocessor controller 44. The implanted TET coil 52 is used to electromagnetically couple the implanted system to an external TET coil 54 and an external power unit and controller 56. In this manner, an external power source can be used to provide power to run the system and/or recharge the batteries.

In the event that both batteries are degradated or depleted, the TET system can supply power to run both stators. To this end, if the batteries are insufficient to power the stators as required, an alarm is activated indicating to the patient that external TET coil 54 should be applied to maintain the operation of the heart pump. This enables the pump to be maintained in operation while the batteries are replaced, recharged or repaired as required.

The TET may be used for communication purposes. Electrical signals to and from the internal microprocessor controller 44 and the external power unit and controller 56 may be sent across the TET coils 52, 54. In use, the external TET coil 54 is positioned on or near the outside of the skin directly or approximately opposite the implanted TET coil 52.

The external power unit and controller 56 can serve several functions and can take various forms. It could be in the form of a belt or a vest and contain rechargeable batteries. It could be or include a table top unit with various visual displays or warning lights and audio alarms connected to the building electrical system through a standard cord and plug.

As represented by the concentric partial circles in FIG. 2, the implanted microprocessor controller 44 could also communicate with an external monitor 58 using radio frequency (RF) waves with RF transmitter/receiver 60. This capability can be designed to require a minimal amount of power and to be used only on demand. The external monitor 58 may or may not be part of or connected to the external power unit and controller 56. The external monitor 58 could take various forms such as a table top unit, a vest and/or even a wrist mounted device designed to look like a wrist watch or a heart rate monitor and having RF communication capabilities for untethered use. The monitor could be used to provide various readouts concerning the operation of the implanted system and could contain various warning indicators.

The implanted microprocessor controller 44 provides the overall control of all functions. As only one internal battery and one motor driver is used at a time, the microprocessor controller 44 selects the battery and driver to be used and through the multiplexer 50 provides power to energize the coils in the stators 24 and 26 in a proper manner and sequence. The microprocessor controller 44 also controls battery charging, distribution and regulation of power received through the TET coil 52, and communicates system data with the external power unit and controller 56 through the TET coil 52 and/or by RF with the monitor 58.

In normal operating mode, the microprocessor controller 44 will configure the system to be powered by a single battery and to run a single motor driver. The microprocessor controller 44 will configure the multiplexer 50 to connect both stators 24, 26 to a single motor driver and will normally run both stators 24, 26 simultaneously. This eliminates the need for connecting the motor stator coils to each other, resulting in an improved level of redundancy. If a motor drive circuit or any of its associated windings or connections fails, the motor can continue running with limited operation. This results in improved reliability.

Because there are dual motor drivers 46, 48, the system can be selfconfigured by the microprocessor controller 44 to utilize a single circuit to control both motor stators. This is the most efficient mode of operation. During this mode of operation, the second driver can be powered down and power may be saved.

If there is a failure of a drive circuit, coil winding or motor connector lead, the system can still run safely and reliably. The motors will be run by a sensorless commutation algorithm based on motor position sensing through back EMF signals and/or motor current signature. This algorithm control can be performed by the microprocessor controller or the motor drive circuits. In this manner, the pump speed can be controlled as desired very accurately.

The microprocessor controller 44 can connect the drive circuit to the motors in virtually any configuration utilizing the multiplexer 50 to provide the best efficiency as well as reliability. The system will provide safe operation during a failure of a motor drive circuit, motor coil, multiplexer circuit or stator connect circuit.

The implanted, inductive TET coil is used to recharge the batteries 40, 42 or to run the system. The recharging will be controlled by microprocessor controller 44. One battery can be recharged while the other is powering the system. This may be advantageous in that the system can provide full battery drain before recharging and improve battery life.

The system can communicate with an outside monitoring system through means of RF telemetry communication and/or pulsed TET coil communication. This allows for easy monitoring and changing of system parameters (battery charge level, motor speed, motor control configurations, etc.).

A wall powered or battery powered charging system will be included in the external power unit and controller 56. It supplies power and communicates with the implanted system through the external TETS coil 54 and the implanted TETS coil 52. Because the external components will be used at least daily to recharge the internal batteries 40, 42, it will be convenient to obtain system performance information regularly. Information regarding battery charging cycles, charging rates and times, discharge rates and times, and recharging rates and times can be stored and used for analysis and prediction of battery performance and battery life. This information can be provided to the patient and medical personnel via the communication and external monitoring and control apparatus. The system can be designed to allow for the external power unit and controller 56 to supply all power and control functions in case of emergencies or when otherwise deemed necessary.

There are a number of failure modes which may occur. This system will operate to reduce or eliminate complications which result.

If a motor coil should short out, an increase in current draw will occur in the motor drive circuit. From this and queries from the microprocessor controller 44, it can be determined which stator has the failure. Upon failure determination, the microprocessor controller 44 can reconfigure the coil connections via the multiplexer 50 so that the short can be by-passed. The pump can continue to operate and a signal or message can be sent to the external monitor 58 and/or the external power unit and controller 56 that this failure has occurred.

If a motor lead or connection become faulty such as by a lead break or insulation failure creating an open or short circuit, the implanted microprocessor controller will sense the failure, reconfigure the connections via the multiplexer 50 and maintain pumping operation.

If a single operating motor drive should fail, the microprocessor controller 44 will sense the failure and reconfigure the system to power the other motor driver circuit and connect it to the stators 24 and 26 via the multiplexer 50 and keep the pump working. A signal can be sent to notify the patient that immediate assistance should be sought due to a system malfunction; however, pumping is maintained.

Because power will normally be drawn from a single battery at any given time, there should exist the opportunity to switch over to the other battery in order to prevent low power failures. The microprocessor controller 44 can constantly monitor the battery voltages and can initiate a change to the other battery whenever needed.

If the microprocessor controller 44 should fail, a motor driver will be provided with a failsafe mode. Upon a microprocessor failure, a motor driver will run in a continuous mode. The patient will be alerted and the failure of the microprocessor controller 44 will be immediately indicated. The patient will be instructed to seek immediate assistance.

The failure of the TET leads and the TET recharging and communication systems can be determined by either the implanted microprocessor controller 44 or the external power unit and controller 56. The patient can be alerted and warned to seek assistance before the batteries fail and the pump ceases to operate.

One benefit of operating in the manner of the present system is that the backup motor driver is available for an emergency but remains powered down during normal operation reducing power consumption. Another benefit is that both motor stators are in operation 100 percent of the time, utilizing maximum torque producing capability of the system. Another benefit is that the battery which is not in use can be in the charging process independently of pump operation. Another benefit is that the external monitor can be activated as desired to monitor system operation.

Although an illustrative embodiment of the invention has been shown and described, it is to be understood that various modifications and substitutions may be made by those skilled in the art without departing from the novel spirit and scope of the present invention.

What is claimed is:

1. An implantable blood pump which comprises:

a pump housing;

a rotor mounted for rotation within said housing, said rotor having an impeller;

first and second stators for aiding in rotation of said impeller;

two stator drivers for driving said stators;

a microprocessor;

a multiplexer for coupling said drivers to said stators in a desired manner, said multiplexer being adapted for coupling either of said drivers to both stators;

first and second batteries;

said batteries, microprocessor and drivers being interconnected and programmed so that during normal operation only one of said batteries is in use at a time for powering both stators simultaneously.

2. An implantable blood pump as defined in claim 1, further comprising an external transcutaneous energy transmission coil and external power source.

3. An implantable blood pump as defined in claim 2, in which said transcutaneous energy transmission coil and external power source are adapted for powering the stators in the event of battery depletion or degradation.

4. An implantable blood pump as defined in claim 3, including an alarm for indicating that a battery problem exists.

5. An implantable blood pump as defined in claim 1, including an external monitor that is RF coupled to said power and control system for untethered user monitoring.

6. An implantable blood pump as defined in claim 5, in which said external monitor comprises a device for mounting on a patient's wrist.

* * * * *